(12) United States Patent
Gutierrez et al.

(10) Patent No.: US 11,510,583 B2
(45) Date of Patent: Nov. 29, 2022

(54) DIAGNOSTIC MASK AND METHOD

(71) Applicant: MEMS START, LLC, Arcadia, CA (US)

(72) Inventors: Roman Gutierrez, Arcadia, CA (US); Tony Tang, Arcadia, CA (US)

(73) Assignee: MEMS START, LLC, Arcadia, CA (US)

( * ) Notice: Subject to any disclaimer, the term of this patent is extended or adjusted under 35 U.S.C. 154(b) by 159 days.

(21) Appl. No.: 16/579,684

(22) Filed: Sep. 23, 2019

(65) Prior Publication Data

US 2020/0093387 A1 Mar. 26, 2020

Related U.S. Application Data

(60) Provisional application No. 62/734,889, filed on Sep. 21, 2018.

(51) Int. Cl.
| | |
|---|---|
| *A61B 5/024* | (2006.01) |
| *H04L 67/12* | (2022.01) |
| *A61B 5/00* | (2006.01) |
| *A61B 3/10* | (2006.01) |

(52) U.S. Cl.
CPC ............ *A61B 5/02438* (2013.01); *A61B 3/10* (2013.01); *A61B 5/0022* (2013.01); *A61B 5/7264* (2013.01); *H04L 67/12* (2013.01)

(58) Field of Classification Search
CPC .............. A61B 5/02438; A61B 5/0022; A61B 5/7264; A61B 3/10; H04L 67/12; H04Q 9/00; H04Q 2209/00; H04Q 2209/10; H04Q 2209/40; H04Q 2209/43; H04Q 2209/70; H04Q 2209/80; H04Q 2209/84
See application file for complete search history.

(56) References Cited

U.S. PATENT DOCUMENTS

| | | | | |
|---|---|---|---|---|
| 6,903,657 | B2 * | 6/2005 | Kwoen | A61B 5/6887 |
| | | | | 128/923 |
| 9,007,216 | B2 * | 4/2015 | Oskin | A61B 5/318 |
| | | | | 340/573.1 |
| 9,740,470 | B2 * | 8/2017 | Shin | H04L 67/2809 |
| 10,004,427 | B1 * | 6/2018 | Shoeb | A61B 5/7221 |
| 10,098,611 | B2 * | 10/2018 | Lee | A61B 7/04 |
| 10,310,296 | B2 * | 6/2019 | Howell | G02C 11/10 |
| 10,332,315 | B2 * | 6/2019 | Samec | G16H 20/70 |
| 10,441,184 | B2 * | 10/2019 | Baumann | A61B 5/361 |
| 10,478,127 | B2 * | 11/2019 | Sampson | A61B 5/0022 |
| 2018/0316781 | A1 * | 11/2018 | Salem | H04L 67/306 |
| 2019/0179409 | A1 * | 6/2019 | Jones | G02B 27/0093 |

* cited by examiner

*Primary Examiner* — Franklin D Balseca

(57) ABSTRACT

A diagnostic mask and method of diagnosing are disclosed. The method includes collecting data from a plurality of sensors in a mask placed on a patient's face such that the mask covers the patient's eyes, the data representing a plurality of health signs of the patient, wherein at least one of the health signs relates to the patient's eyes; and transmitting a signal from the mask, the signal representing the data representing the plurality of health signs.

16 Claims, 10 Drawing Sheets

DIAGNOSTIC MASK AND METHOD

REFERENCE TO RELATED APPLICATIONS

The present application claims priority to U.S. Provisional Patent Application No. 62/734,889, filed Sep. 21, 2018, entitled "Diagnostic Mask and Method of Diagnosing," the disclosure thereof incorporated by reference herein in its entirety.

TECHNICAL FIELD

The present disclosure is generally related to medical sensing devices. More particularly, the present disclosure is directed to systems and methods for automatically collecting health data from patients using medical sensing devices.

BACKGROUND

There are numerous commercially-available medical sensing devices on the market. These devices generally include a medical sensor, for example such as an infrared thermometer, a photoplethysmography (PPG or optical heart rate monitor), an oximeter, a pupillometer, an electrocardiogram (EKG or ECG) sensor, an electroencephalogram (EEG) sensor, a blood pressure monitor, and the like. However, these sensing devices are sold as separate products that are often expensive and not portable. This creates several issues. First, it takes too long to take measurements by using one device after another. Second, it requires owning and carrying a whole series of medical devices, which is not practical. Furthermore, the data from the separate medical devices is not easily integrated and calibrated, making it difficult to diagnose medical conditions that require measurements from multiple instruments. As a result, consumers currently do not have a medical device available that can diagnose a wide range of conditions. For example, when a person passes out and wakes up or complains of common ailments such as headache, dizziness, etc., we do not have the tools to determine whether the person should be taken to an emergency room or be left alone to rest. There is a need in the art for a consumer medical device that is portable, easy to use, and can accurately diagnose a wide range of medical conditions objectively.

BRIEF DESCRIPTION OF THE DRAWINGS

Further aspects of the present disclosure will be more readily appreciated upon review of the detailed description of the various disclosed embodiments, described below, when taken in conjunction with the accompanying figures.

DETAILED DESCRIPTION OF THE EMBODIMENTS

Diagnostic masks, and methods of diagnosing a patient using the diagnostic masks, are disclosed. The mask may include a number of sensors that measure health signs including the vital signs (temperature, heart rate, blood pressure, and breathing rate), physiological responses (for example, sweat, pupillary, and muscular), and physical characteristics (for example, sclera color, blood vessel distribution, skin color and reflectivity, and ocular movements). The mask may include a number of components (for example LEDs, displays, speakers, electrodes) that provide stimuli (for example light, patterns, images, sound, and electrical signals) to obtain reactions from the patient. In some embodiments, the mask provides one or more diagnoses and/or recommendations to the patient. In some embodiments, the mask transmits the health signs to a remote device that provides one or more diagnoses and/or recommendations. For example, a doctor may use a tablet to review the health signs, and to provide a recommendation and/or diagnosis.

Figure 1:
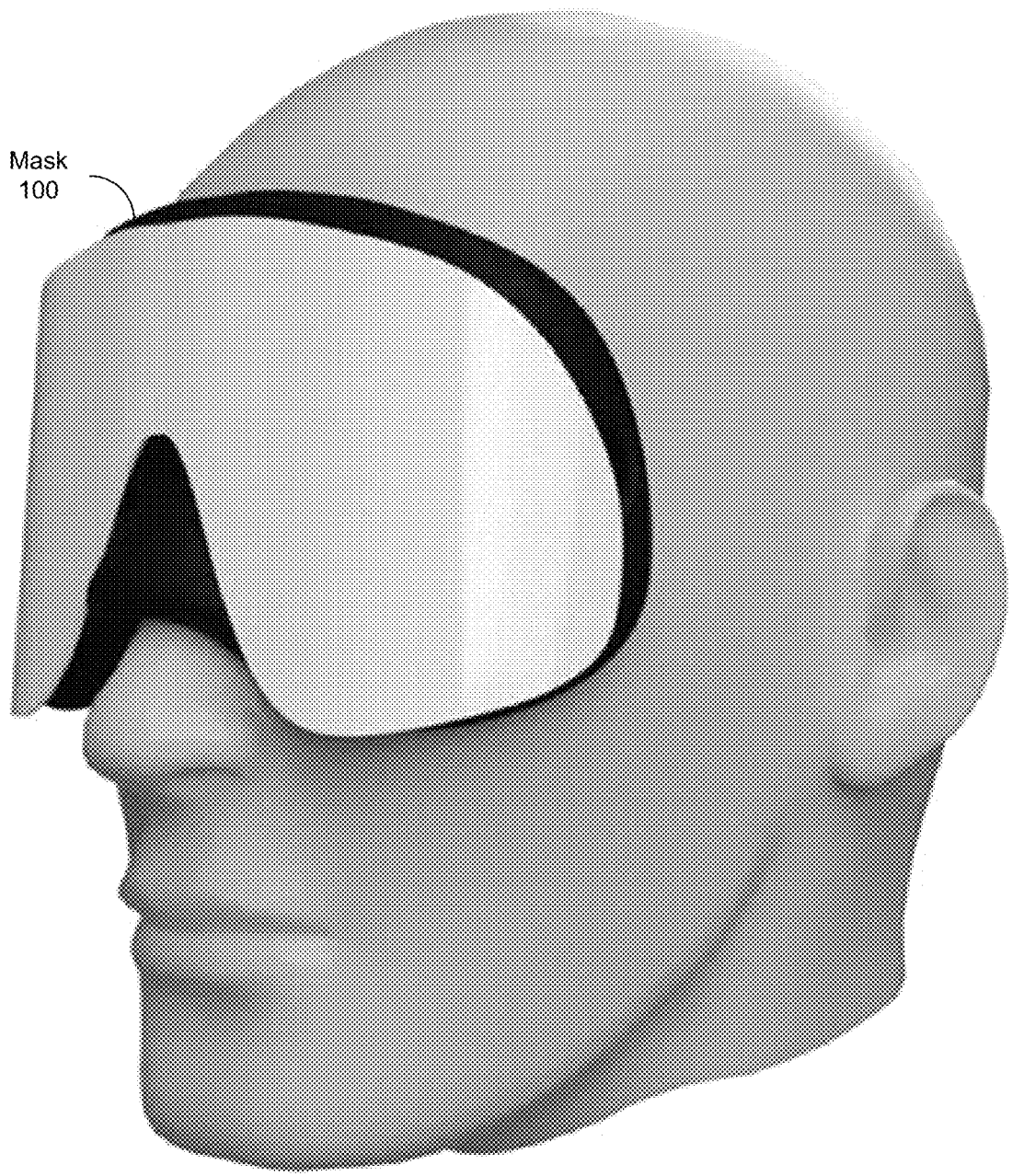
FIG. 1 illustrates a patient wearing a diagnostic mask according to some embodiments of the disclosed technology.

FIG. 1 illustrates a patient wearing a diagnostic mask 100 according to some embodiments of the disclosed technology. In some embodiments, the mask 100 covers the eyes, a portion of the forehead, and a portion of the nose. In some embodiments, the mask 100 may be secured to the face of the patient by a strap or the like.

Figure 2:
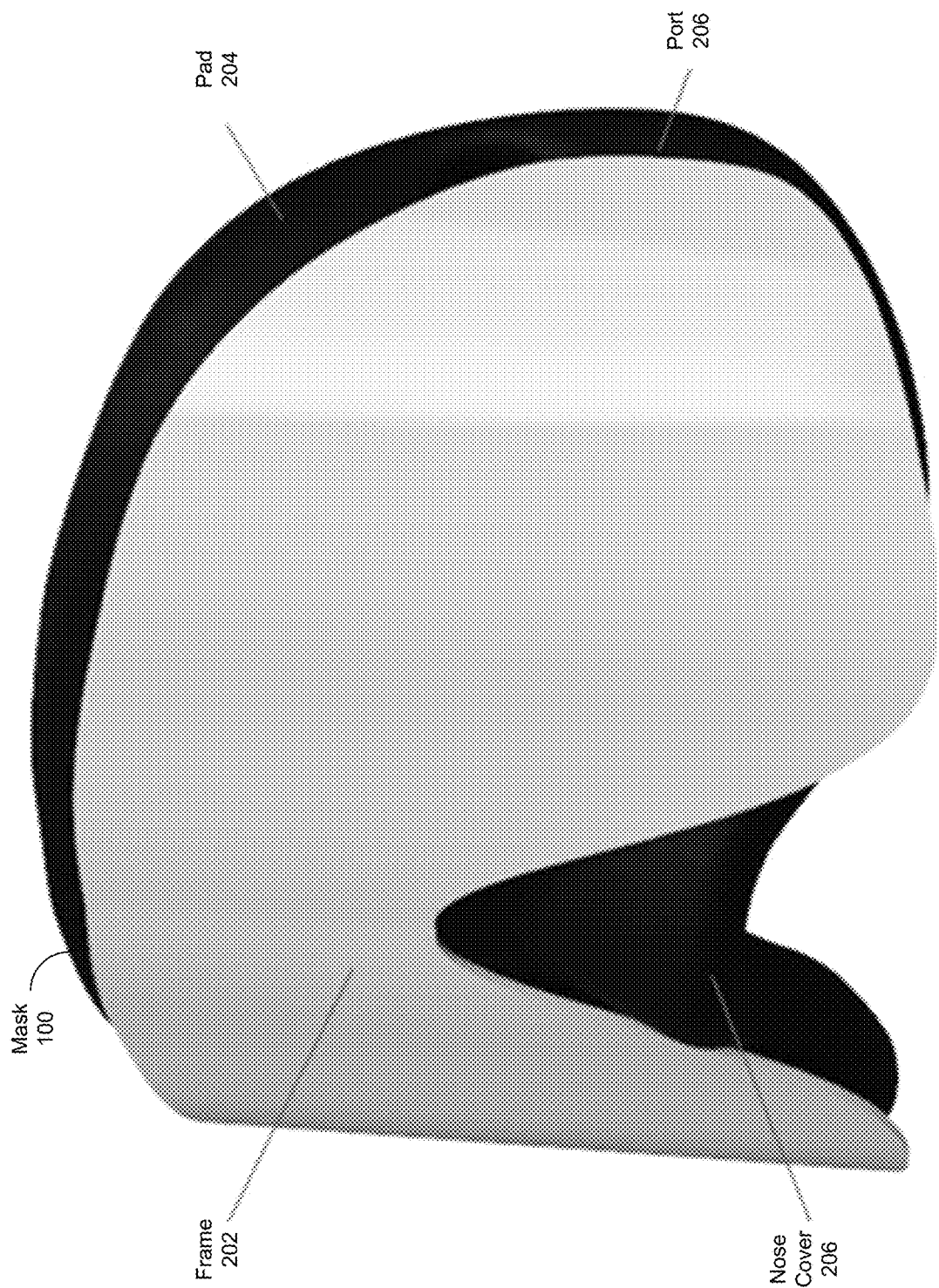
FIG. 2 illustrates an external portion of the mask according to some embodiments of the disclosed technology.

FIG. 2 illustrates an external portion of the mask 100 according to some embodiments of the disclosed technology. Referring to FIG. 2, the mask may include a rigid frame 202. In some embodiments, the rigid frame 202 may be bent to better conform to the face of the patient. The frame 202 may be fabricated from a material that prevents light from reaching the patient's eyes when the mask 100 is worn. In some embodiments, the frame 202 may act as a display screen to provide diagnoses, recommendations, and the like to the patient, for example in the form of text, images, video, and the like. In some embodiments, an interior surface of the frame 202 is visible to the patient as a display screen. In some of these embodiments, information shown to the patient on the interior surface of the frame 202 is also visible on the exterior surface of the frame 202.

The diagnostic mask 100 may include a pad 204 that is attached to the frame 202. The pad 204 may be fabricated from an elastic material such as foam or the like. The pad 204 may be easily deformable so as to conform to a face of the patient. Together, the frame 202 and pad 204 may prevent light external to the mask 100 from reaching the eyes of the patient. The pad 204 may be fabricated from a soft material so the mask 100 is comfortable to wear.

The diagnostic mask 100 may include a nose cover 206. The nose cover 206 may cover a portion of the patient's nose. The nose cover 206 may include sensors to detect respiration of the patient. The sensors may be implemented as microphones, for example.

The diagnostic mask 100 may include a port 208 configured to receive an electrical connector. The port 208 may allow for charging a rechargeable battery of the mask 100. The port 208 may allow for wired communications between the mask 100 and external devices. In some embodiments, the port 208 may be implemented as a micro-USB connector.

Figure 3:
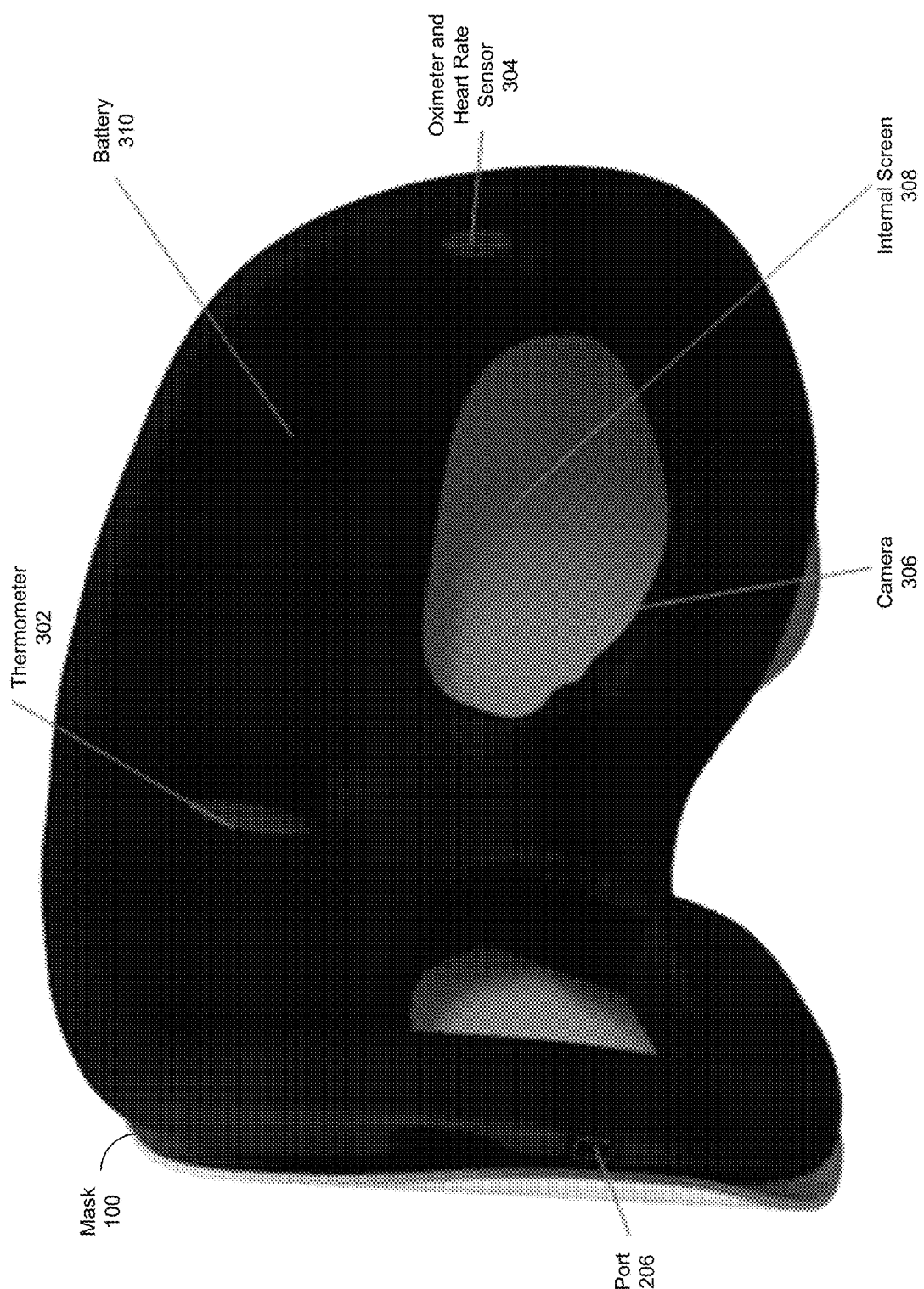
FIG. 3 illustrates an interior portion of the diagnostic mask according to some embodiments of the disclosed technology.

FIG. 3 illustrates an interior portion of the diagnostic mask 100 according to some embodiments of the disclosed technology. Referring to FIG. 3, the mask 100 may include a thermometer 302 configured to obtain a temperature of the patient. The thermometer 302 may be implemented as a thermal infrared (IR) sensor.

The diagnostic mask 100 may include an oximeter and heart rate sensor 304. The sensor 304 may be implemented as an optical sensor. The sensor 304 may measure blood flow and oxygenation of the patient.

The diagnostic mask 100 may include one or more cameras 306. In some embodiments, two cameras may be used to image both eyes while they are illuminated by light sources within the mask. The light sources may be implemented as light-emitting diodes (LEDs). In some embodiments, the LEDs may operate near infrared so they are not visible to the eye, but are visible to the camera. These embodiments facilitate imaging the eye without affecting the pupillary response and better differentiate the pupil from the iris compared with visible light. In some embodiments, some of the illumination LEDs may operate in the visible light spectrum (e.g. white, red, green, or blue) so as to affect the pupillary response.

The cameras may be used to track eye movement, size of the pupil, and other characteristics of the eyes the patient. Visible LEDs placed at different positions or sounds may be used to cause the patient's eyes to move while the camera tracks the motion. Arrays of LEDs or displays may be used as well. The LEDs may include lenses, diffraction gratings, diffusers, polarizers, or other optical elements to shape or pattern the light emitted by the LEDs.

In some embodiments, LEDs of different colors are used to detect conditions that affect the color sensitivity of the eyes (e.g. glaucoma). The cameras may also look at other characteristics of the eye that may indicate the presence of a medical illness, disorder or condition. These characteristics may include specific features or coloring of the iris, redness or yellowing of the sclera (that is, the white part of the eye), puffiness of eyelids, dryness of the eyes, and the like.

The diagnostic mask 100 may include one or more internal display screens 308. The internal display screens 308 may be used for displaying light as a stimulus for the patient. The internal display screens 308 may be used to display information to the patient, for example such as instructions, status of the mask 100, status of the diagnostic procedure, diagnoses, recommendations, and the like.

The diagnostic mask 100 may include one or more batteries 310. The batteries 310 may be rechargeable. For example, the batteries 310 may be implemented as lithium-ion batteries. In some embodiments, the batteries 310 may be recharged using the port 208 in the mask 100.

The diagnostic mask 100 may include further features, for example as described below.

Figure 4:
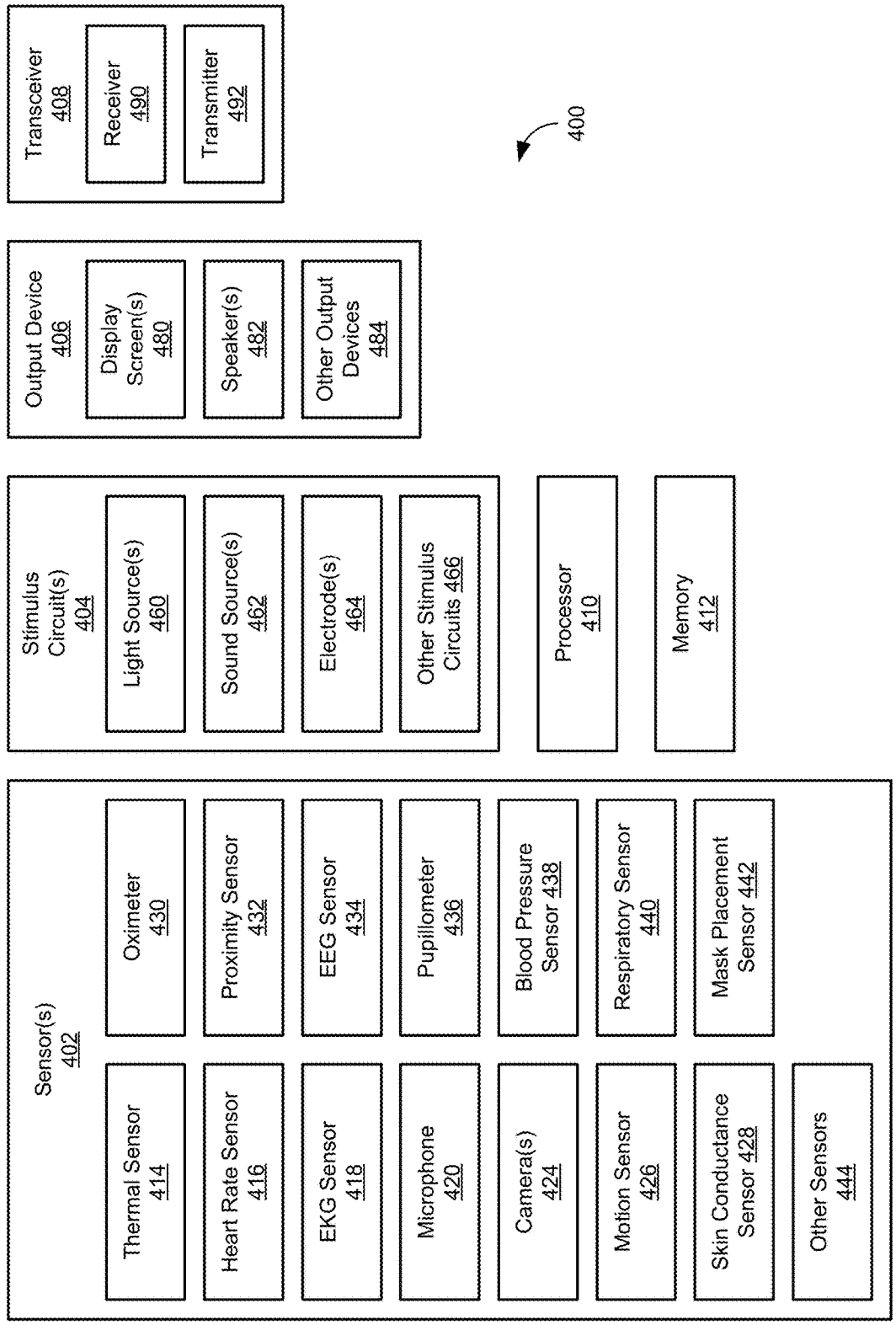
FIG. 4 is a block diagram of a diagnostic mask according to some embodiments of the disclosed technology.

FIG. 4 is a block diagram of a diagnostic mask 400 according to some embodiments of the disclosed technology. Embodiments of the diagnostic mask 400 may include other elements, for example such as those described elsewhere in this disclosure. It should be understood that various embodiments of the disclosed technology may employ any combination of the features described herein.

Referring to FIG. 4, the diagnostic mask 400 may include one or more sensors 402, one or more stimulus circuits 404, an output device 406, a transceiver 408, a processor 410, and a memory 412. The sensors 402 may include a thermal sensor 414, for example to measure a skin temperature of the patient. The sensors 402 may include a heart rate sensor 416 to measure a heart rate of the patient. The sensors 402 may include an electrocardiogram (EKG) sensor 418 to measure heart activity of the patient. The sensors 402 may include a microphone 420. The microphone 420 may be placed near the nose of the patient to measure the patient's respiratory activity. The microphone 420 may be used to receive speech of the patient, for example to control the diagnostic mask 400, to respond to prompts provided by the diagnostic mask 400, and the like.

The sensors 402 of the diagnostic mask 400 may include one or more cameras 424. The cameras 424 may operate as described above with reference to the cameras 306 of the diagnostic mask 100 of FIG. 3.

The sensors 402 of the diagnostic mask 400 may include a motion sensor 426 to record motion of the patient. The motion sensor 426 may be implemented as inertial sensors such as accelerometers, gyroscopes, and the like.

The sensors 402 of the diagnostic mask 400 may include a skin conductance sensor 428 to sense sweat production response of the patient. The sensors 402 may include an oximeter 430. The oximeter 430 may operate as described above with reference to the oximeter and heart rate sensor 304 of the diagnostic mask 100 of FIG. 3.

The sensors 402 of the diagnostic mask 400 may include a proximity sensor 432. The sensors 402 may include an electroencephalograph (EEG) sensor 434 to measure the patient's brain activity. In some embodiments, the EKG sensor 418 and the EEG sensor 434 may use the same electrodes to measure the skin potential, and filtering algorithms may be used to separate the heart and brain electrical signals.

The sensors may include a pupillometer 436. The sensors 402 may include a blood pressure sensor 438 to record the patient's blood pressure. The sensors 402 may include a respiratory sensor 440 to record the respiration of the patient.

The sensors 402 of the diagnostic mask 400 may include a mask placement sensor 442 to detect a placement of the mask 400 on the patient. The detected placement may be used to guide the patient in the placement of the mask 400, as described below. The sensors 402 may include other sensors 444.

The stimulus circuits 404 of the diagnostic mask 400 may include one or more light sources 460. The light sources may include LEDs and may be employed as described above. The stimulus circuits 404 may include one or more sound sources 462. The sound sources 462 may include speakers, tone generators, buzzers, and the like. In some embodiments, sound and/or light excitation may be provided to the patient while motion of the patient is being sensed to determine the patient's movement response to sounds and/or lights.

The stimulus circuits 404 of the diagnostic mask 400 may include one or more electrodes 464 for providing electrical stimulus to the patient. In some embodiments, the electrodes 464 provide physical pain input to the patient while the sensors 402 record the response.

The output device 406 of the diagnostic mask 400 may include one or more display screens 480. In some embodiments, the display screens 480 may be implemented within the frame 202 of the diagnostic mask 100 of FIG. 2 as an external display screen, inside the mask 100 as the internal screen 308 of FIG. 3, and the like. The display screens 480 may be fabricated using any suitable technology. For example, the internal screen 308 may be fabricated as a liquid-crystal display (LCD), and the external screen may be fabricated as an organic light-emitting diode (OLED) screen. In some embodiments, the display screens 480 may display images captured by the cameras (e.g. images of the patient's eyes), extracted parameters from the various sensor data (e.g. heart rate, body temperature, oxygen level, and pupillary response), as well as diagnoses and/or recommendations for the patient.

The output devices 406 of the diagnostic mask 400 of FIG. 4 may include one or more speakers 482. The speakers 482 may provide aural stimuli to the patient. The speakers 482 may provide information to the patient, for example as described above. The output devices 406 of the diagnostic mask of FIG. 4 may include other output devices 484 as well.

The transceiver 408 of the diagnostic mask 400 of FIG. 4 may include a transmitter 492. The transmitter 492 may be employed to transmit data recorded by the sensors 402 to a remote device for generating diagnoses and/or recommendations. In embodiments where the diagnostic mask 400 generates the diagnoses and/or recommendations, the transmitter 492 may be employed to transmit the diagnoses and/or recommendations to external electronic devices, for example such as a smart phone, tablet, and the like.

The transceiver 408 of the diagnostic mask 400 of FIG. 4 may include a receiver 490. In embodiments where diagnoses and/or recommendations are generated by an external device, the receiver 490 may be employed to receive those diagnoses and/or recommendations into the mask 400. The mask 400 may then provide that information to the patient. The receiver 490 may be used to receive firmware updates for the mask 400.

The transceiver 408 may be implemented using any suitable technology. The transceiver 408 may employ a wired protocol to exchange data using the port 208 of the mask 100 of FIG. 2. The transceiver 408 may employ a wireless protocol to exchange data. Any wireless protocol may be used, for example such as Bluetooth, Wi-Fi, and the like.

The memory 412 of the diagnostic mask 400 of FIG. 4 may be used to store data, processor instructions, and the like. The processor 410 may operate according to the instructions stored in the memory 412.

Figure 5:
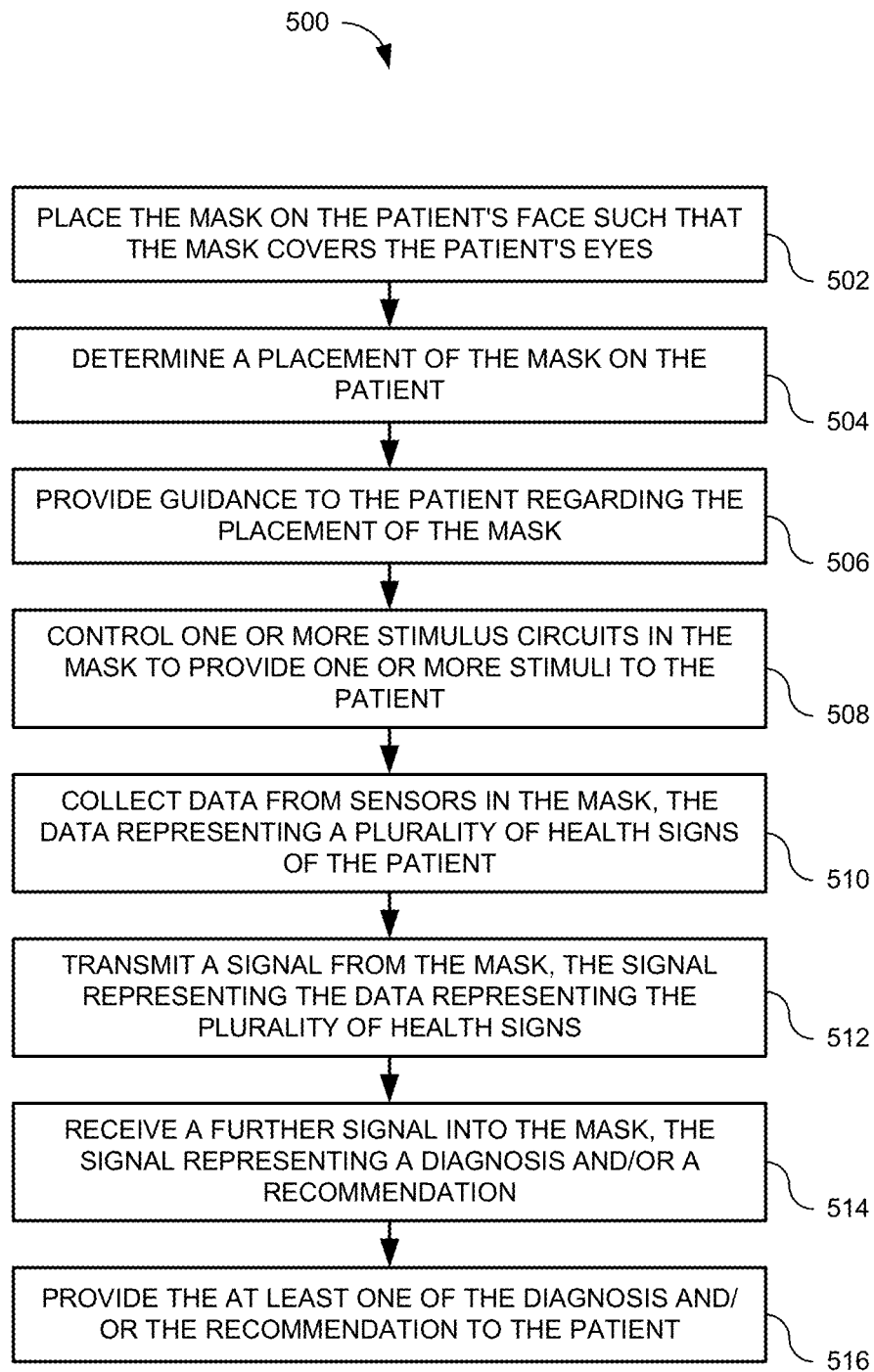
FIG. 5 illustrates a process for the disclosed diagnostic masks according to some embodiments of the disclosed technology.

FIG. 5 illustrates a process 500 for the disclosed diagnostic masks according to some embodiments of the disclosed technology. Depending on the implementation, the process 500 may include additional, fewer, or alternative elements, and the elements may be performed in various orders or in parallel.

Referring to FIG. 5, the process 500 may include placing the mask on the patient's face such that the mask covers the patient's eyes, at 502. The mask may be placed on the patient's face by a doctor, by an assistant, or by the patient.

The process 500 may include determining a placement of the mask on the patient, at 504. In the example of FIG. 4, sensors 402 such as the proximity sensor 432 and the mask placement sensor 442 may automatically determine the placement of the mask. In some embodiments, these sensors may be combined into a single sensor.

Referring again to FIG. 5, the process 500 may include providing guidance to the patient regarding the placement of the mask, at 506. For example, responsive to detecting an improper placement of the mask on patient, the mask may prompt the patient to adjust the mask.

The process 500 may include controlling one or more stimulus circuits in the mask to provide one or more stimuli to the patient, at 508. In the example of FIG. 4, one or more of the stimulus circuits 404 may provide stimuli to the patient, for example such as light, sound, electrical stimulus, and the like.

Referring again to FIG. 5, the process 500 may include collecting data from the sensors in the mask, at 510. The data may represent a plurality of health signs of the patient. At least one of the health signs may relate to the patient's eyes. In the example of FIG. 4, the processor 410 may receive data collected by the sensors 402. In some examples, the sensors 402 may collect the data while the stimulus circuits 404 are providing stimuli to the patient, in order to measure the patient's response to the stimuli.

Referring again to FIG. 5, the process 500 may include transmitting a signal from the mask, where the signal represents the data representing the plurality of health signs, at 512. In the example of FIG. 4, the signal may represent the data collected by the sensors 402 of the mask 400 and may be transmitted by the transmitter 492 of the transceiver 408 to a remote device. The remote device may generate diagnoses and/or regulations based on the transmitted health signs.

In some embodiments, the remote device provides the transmitted health signs to a medical professional, who provides diagnoses and/or recommendations. For example, a doctor may receive the health signs collected from a patient using a computer, smartphone, tablet, or the like. The doctor may evaluate the patient using the health signs. The doctor may determine one or more diagnoses and/or recommendations for the patient and may enter the diagnoses and/or recommendations into the device. The device may transmit the diagnoses and/or recommendations to the patient. For example, the device may transmit the diagnoses and/or recommendations to the mask and/or to other devices used by the patient. The device(s) may then provide the diagnoses and/or recommendations to the patient.

Referring again to FIG. 5, the process 500 may include receiving a further signal into the mask, where the further signal represents the diagnosis and/or a recommendation, at 514. The diagnosis and/or recommendation may be determined based on the health signs previously transmitted from the mask. Processes for determining the diagnoses and/or recommendations based on health signs are described in detail below. In the example of FIG. 4, the further signal may be received by the receiver 490 of the transceiver 408.

Referring again to FIG. 5, the process 500 may include providing diagnoses and/or recommendations to the patient, at 516. In the example of FIG. 4, the diagnoses and/or recommendations may be provided by one or more of the output devices 406. The information may be provided by the internal or external display screens 480, for example in the form of text, images, video, and the like. The information may be provided by the speakers 482, for example in the form of an audio presentation. The information may be provided by both the display screens 480 and the speakers 482, for example in the form of a multimedia presentation.

Referring again to FIG. 5, the process 500 or elements thereof may be repeated as necessary. For example, the process 500 may be employed to provide continuous or continual monitoring of the patient over a specified interval.

Figure 6:
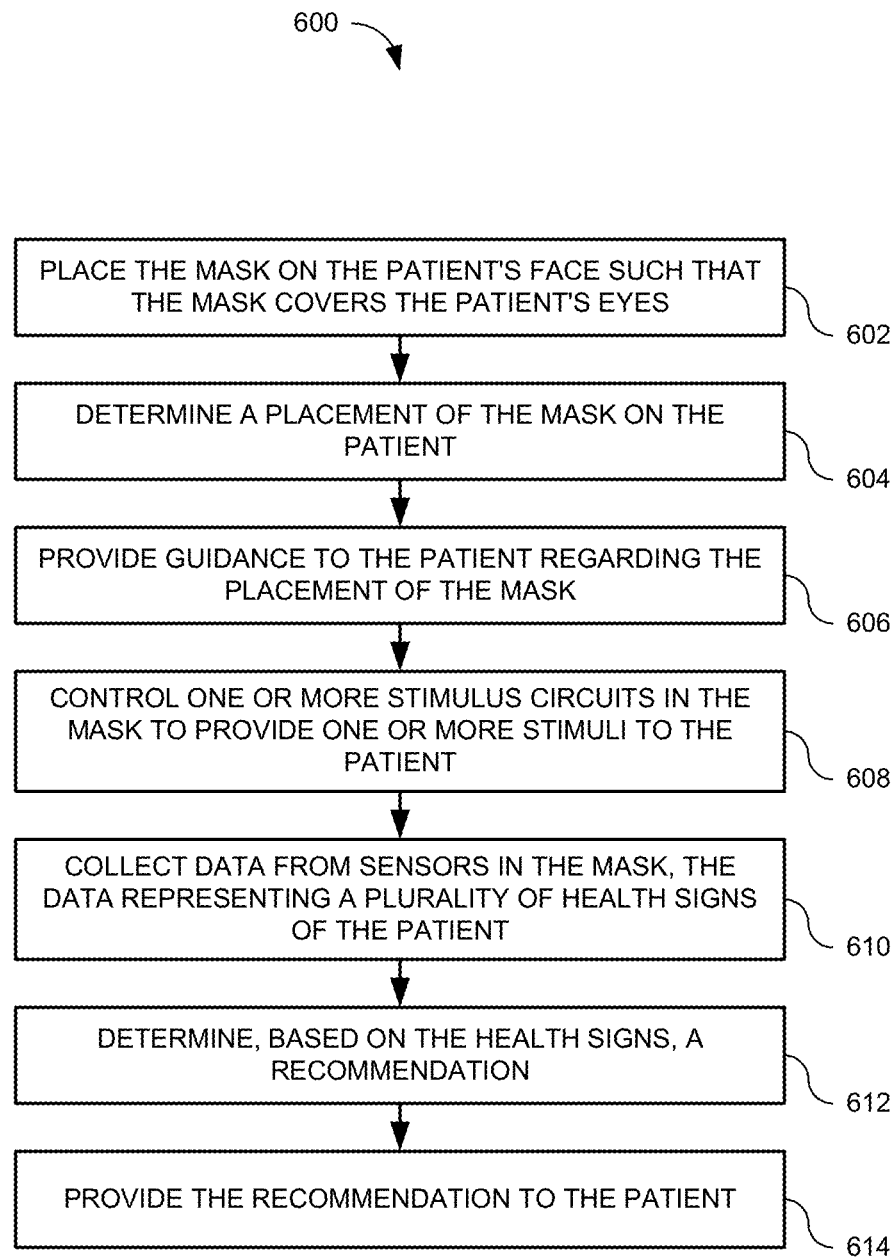
FIG. 6 illustrates a process for the disclosed diagnostic masks according to some embodiments of the disclosed technology.

FIG. 6 illustrates a process 600 for the disclosed diagnostic masks according to some embodiments of the disclosed technology. Depending on the implementation, the process 600 may include additional, fewer, or alternative elements, and the elements may be performed in various orders or in parallel.

Referring to FIG. 6, the process 600 may include placing the mask on the patient's face such that the mask covers the patient's eyes, at 602. The mask may be placed on the patient's face by a doctor, by an assistant, or by the patient.

The process 600 may include determining a placement of the mask on the patient, at 604. In the example of FIG. 4, sensors 402 such as the proximity sensor 432 and the mask placement sensor 442 may automatically determine the placement of the mask. In some embodiments, these sensors may be combined into a single sensor.

Referring again to FIG. 6, the process 600 may include providing guidance to the patient regarding the placement of the mask, at 606. For example, responsive to detecting an improper placement of the mask on patient, the mask may prompt the patient to adjust the mask.

The process 600 may include controlling one or more stimulus circuits in the mask to provide one or more stimuli to the patient, at 608. In the example of FIG. 4, one or more of the stimulus circuits 404 may provide stimuli to the patient, for example such as light, sound, electrical stimulus, and the like.

Referring again to FIG. 6, the process 600 may include collecting data from the sensors in the mask, at 610. The data may represent a plurality of health signs of the patient. At least one of the health signs may relate to the patient's eyes. In the example of FIG. 4, the processor 410 may receive data collected by the sensors 402. In some examples, the sensors 402 may collect the data while the stimulus circuits 404 are providing stimuli to the patient, in order to measure the patient's response to the stimuli.

Referring again to FIG. 6, process 600 may include determining one or more recommendations based on the collected health signs, at 612. In the example of FIG. 4, the recommendations may be determined by processor 410 based on data representing health signs collected by the sensors 402 and stored in the memory 412. Processes for determining the recommendations based on health signs are described in detail below.

Referring again to FIG. 6, the process 600 may include providing recommendations to the patient, at 614. In the example of FIG. 4, the recommendations may be provided by one or more of the output devices 406. The information may be provided by the internal or external display screens 480, for example in the form of text, images, video, and the like. The information may be provided by the speakers 482, for example in the form of an audio presentation. The information may be provided by both the display screens 480 and the speakers 482, for example in the form of a multimedia presentation.

Referring again to FIG. 6, the process 600 or elements thereof may be repeated as necessary. For example, the process 600 may be employed to provide continuous or continual monitoring of the patient over a specified interval.

Figure 7:
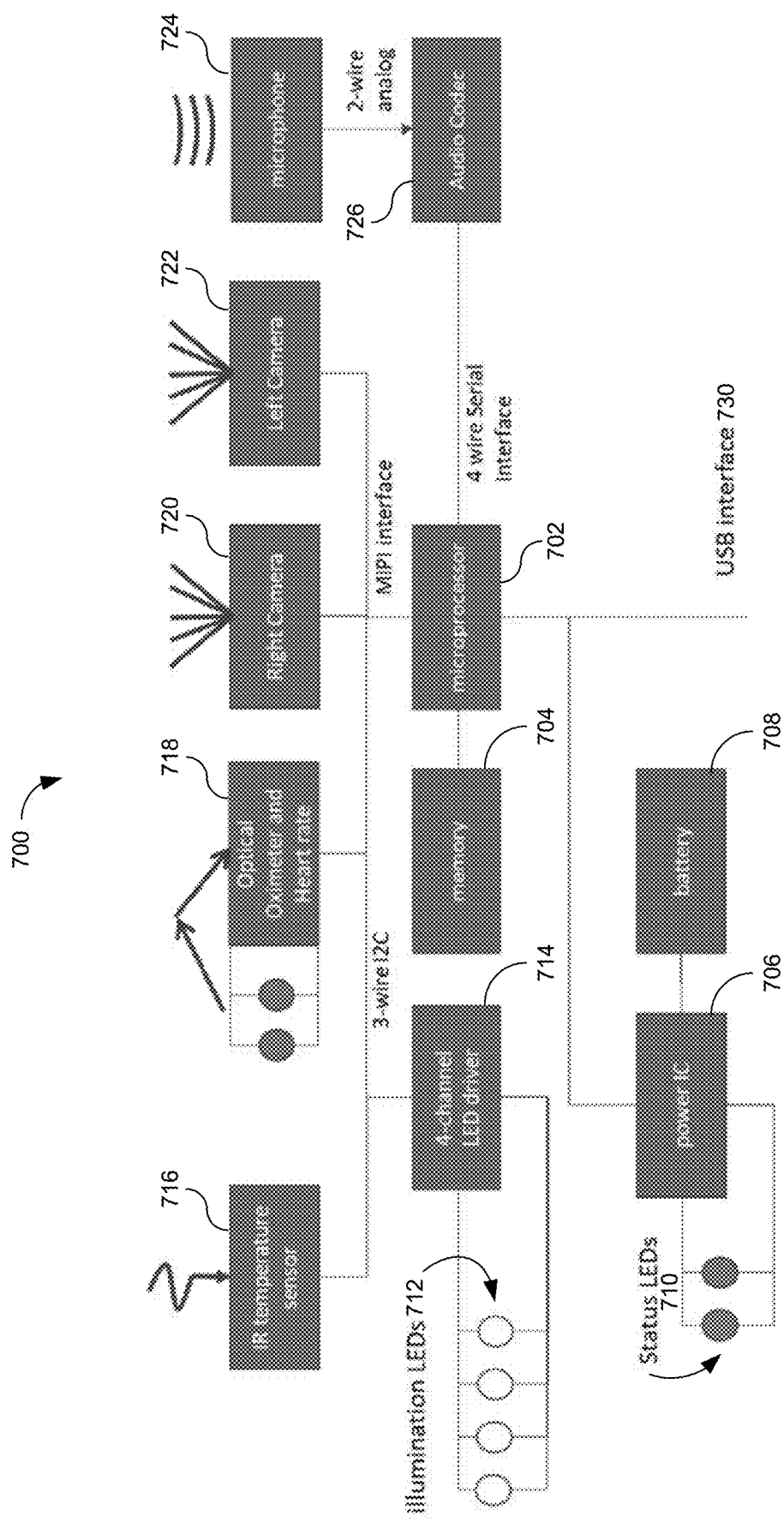
FIG. 7 is a block diagram of a diagnostic mask according to some embodiments of the disclosed technology.

FIG. 7 is a block diagram of a diagnostic mask 700 according to some embodiments of the disclosed technology. Referring to FIG. 7, the diagnostic mask 700 may include a microprocessor 702, and a memory 704. The memory 704 may store the collected health signs of the patient, diagnoses and recommendations for the patient, and instructions executable by the microprocessor 702 to perform the functions disclosed herein.

The diagnostic mask 700 of FIG. 7 may include one or more status LEDs 710. The status LEDs 710 may be employed to indicate operational status of the diagnostic mask 700, status of the processes executed by the mask 700, and other information. The status LEDs 710 may be visible from inside the mask 700, outside the mask 700, or both.

The diagnostic mask 700 of FIG. 7 may be powered by one or more batteries 708 which may be rechargeable, making the mask 700 portable. The mask 700 may include a power integrated circuit (IC) 706 to provide the correct voltages to other components of the mask 700, for example by providing voltage conversion, and the like.

The diagnostic mask 700 of FIG. 7 may include one or more in the illumination LEDs 712 located inside the mask 700 to provide stimuli to the patient, and the like. The mask 700 may include an LED driver to drive the illumination LEDs 712. In the example of FIG. 7, the LED driver may be implemented as a 4-channel LED driver 714. The processor 702 may be used to command how all of the LEDs are turned on and off.

The diagnostic mask 700 of FIG. 7 may include an infrared (IR) temperature sensor 716. The IR temperature sensor 716 may be employed to measure a temperature of the patient, and the like.

The diagnostic mask 700 of FIG. 7 may include an optical oximeter and heart rate monitor 718. The optical oximeter and heart rate monitor 718 may be employed to measure the patient's oxygen level, heart rate, and the like. Sensors other than audio and video sensors may be connected to the microprocessor over a 3-wire inter-integrated circuit (I2C) interface. In the example of FIG. 7, both of the IR temperature sensor 716, and the optical oximeter and heart rate monitor 718, are connected to the microprocessor 702 by an I2C interface.

The diagnostic mask 700 of FIG. 7 may include a plurality of cameras. In the example of FIG. 7, the mask 700 includes a right camera 720 for the right eye, and a left camera 722 for the left eye. The cameras 720, 722 may communicate with the microprocessor 702 over a mobile industry processor interface (MIPI) bus, or the like.

The diagnostic mask 700 of FIG. 7 may include a microphone 724 to capture sound from the patient, for example such as the patient's speech. Signals generated by the microphone 724 in response to sound may be provided to an audio codec 726 over a 2-wire analog interface. The audio codec 726 may encode the sound as audio signals and transmit the encoded signals to the microprocessor 702 over a 4-wire inter-integrated circuit sound (I2S) serial interface.

The diagnostic mask 700 of FIG. 7 may include a universal serial bus (USB) interface 730. The diagnostic mask 700 may communicate with external devices over the USB interface 730. The battery 708 may be charged over the USB interface 730.

In some embodiments, the mask includes a central processor. The central processor may receive the signals from all of the sensors and may process the signals to extract valuable information. In order to reduce test time and have data from various sensors at the same time, the system may be designed to gather data from all sensors simultaneously. Some of the data may be processed in real time, while other data may be saved for processing once all the data has been collected. In the example of FIG. 7, the cameras 720, 722 may be connected to the processor 702 directly through a multi-channel high speed serial interface (e.g. MIPI), while the other sensors are connected through an I2C bus, and the sound audio codec is connected with an I2S bus.

In order to avoid losing data caused by conflicts in any shared bus, buffers may be used to store some data prior to sending to the processor. The duration of data collected may be 15 seconds for example, and may range from a few seconds to more than one minute. The data may then be processed to extract relevant information. For example, for the optical oximeter and heart rate sensor, the data may be passed through a filter and data processing to detect the heart rate and oxygen level using methods known to those skilled in the art. The images from the camera may be processed to identify the iris and determine its location and size, using methods known by those skilled in the art such as edge detection, and fitting a circle to the edge to determine the center and radius of the circle.

The data from the microphone may be used to determine the patient's breathing rate by filtering the signal to isolate the breathing sound and identifying when the patient is breathing. The data from the IR temperature sensor may be processed to compensate for ambient temperature and averaged to ensure the most accurate reading possible.

One or more of the sensors may be used to determine when the mask is being used on a patient so that the measurement can begin automatically without having to press a button. For example, the IR temperature sensor may detect the heat from the forehead of the patient when the temperature exceeds a certain value. The cameras may detect the presence of the patient's eyes. The optical oximeter and heart rate sensor may detect the presence of hemoglobin in the blood underneath the skin. A proximity sensor may be used for this purpose. These sensors may also be used to ensure the mask is positioned correctly and provide feedback to the patient when it is not. For example, if the mask is not pressed against the face, there may be excessive light leaking into the cameras, which would affect the pupil measurement. The processor may be used to sense this condition by detecting image brightness with all LEDs turned off and warn the patient to press the mask a little bit more. Once the processor successfully captures and filters the data from all the sensors, the processor (or a separate GPU/graphic processor unit or processor) may be used to diagnose the problem with the patient by combining the data from all of the sensors.

In one embodiment, the diagnosis may be done using data processing. Certain parameters are extracted from the filtered data and compared with stored values related to specific conditions. For example, a concussed patient will have slower pupil response to light than a healthy patient. Therefore, the processor may extract the pupil size as a function of time from the series of images collected by the camera. Then, the processor may determine how quickly the pupil responded to the light excitation. In addition, depending on the damage to the brain and the portion of the brain that is damaged, the heart rate or even the temperature of the patient may be affected. The processor may take the optical signal collected by the optical heart rate sensor and extract the heart rate as well as the variation in the heart rhythm. The processor may take the signal from the electrocardiogram sensor to determine the delay in blood reaching the head to determine blood pressure and other blood flow parameters. By taking all of these into account, an improved diagnosis of the underlying condition may be made, which could later be confirmed by doctors using more sophisticated non-portable equipment at the hospital or doctor's office.

In one embodiment, the diagnosis is performed using artificial intelligence (AI). The filtered data may be fed into a neural network that has been trained to detect the various conditions. The neural network may be a multilayer neural network for deep learning using training data. For example, hundreds to thousands of patients with known conditions may be evaluated with this instrument to record all relevant filtered data. A portion of this large patient data set may then be used to train the neural network to recognize the various conditions. Then, the remaining patient data may be used to confirm that the neural network is able to properly classify the various conditions. Due to the large number of operations that neural networks require, these calculations may be performed in a multicore processor, but may be better suited to GPUs, FPGAs, or other architectures designed for parallel processing.

In some embodiments, the processor for artificial intelligence resides inside the mask.

In some embodiments, the data is sent from the mask to a server in the cloud where the neural network processing may be done, reporting the diagnosis back to the mask. The mask may transmit the data to the cloud via a smartphone or tablet. For example, the mask may include a wireless interface (e.g. Bluetooth, Wi-Fi) to send the data to an app on the smartphone. Then, the app may communicate with the server in the cloud via the smartphone's Wi-Fi or the broadband cellular network.

In some embodiments, both of these diagnosis methods may be used in combination to improve the accuracy of the diagnosis as well as to explain the diagnosis.

Figure 8:
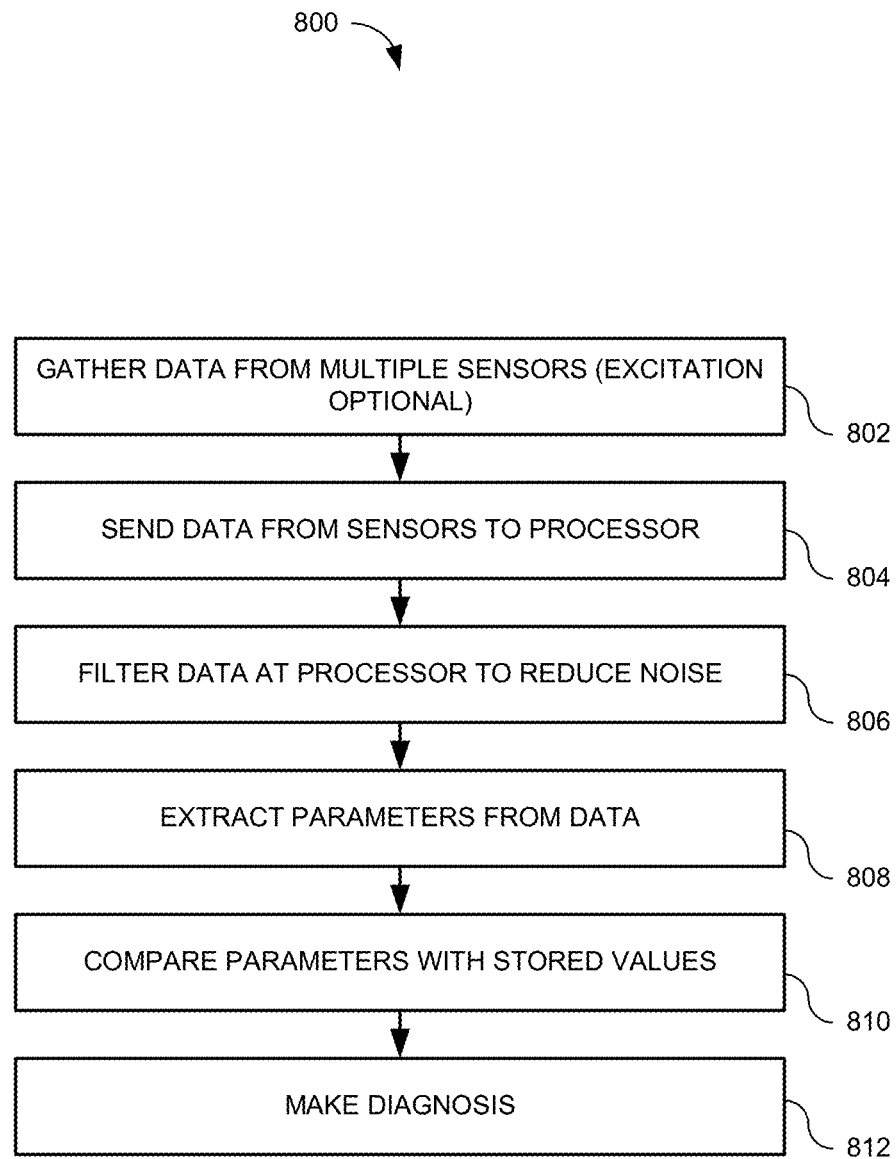
FIG. 8 illustrates a process for generating diagnoses and/or recommendations using data processing according to embodiments of the disclosed technology.

FIG. 8 illustrates a process 800 for generating diagnoses and/or recommendations using data processing according to embodiments of the disclosed technology. Depending on the implementation, the process 800 may include additional, fewer, or alternative elements, and the elements may be performed in various orders or in parallel.

Referring to FIG. 8, the data from various sensors is collected for a determined period of time, at 802. For example, the determined period of time may be around 15 seconds but could be as short as one second or as long as one minute or more. While the data is being collected, the mask may provide light, sound or other types of excitation of the patient's senses that may be used to determine patient response to various stimuli. This data may be stored in a buffer.

The data from the sensors may be sent to the processor along with a time stamp that keeps the data synchronized in time, at 804. The data may be filtered at the processor to reduce noise in order to uncover the important underlying signals, at 806.

Parameters are extracted from the filtered data, at 808. For example, the size of the pupil and motion of the eye may be extracted from the series of images captured during the test. The heart rate or blood pressure may be extracted from the optical signal versus time of the optical heart rate sensor and/or the electrical signal of the electrocardiogram sensor.

The extracted parameters may be compared with stored values corresponding to healthy levels as well as levels that indicate particular conditions, at 810. For example, a patient with normal pupillary response, high body temperature and fast pulse rate may be suffering from heat stroke, while a patient with slow pupillary relaxation response, high body temperature and fast pulse rate may be suffering from concussion.

Figure 9:
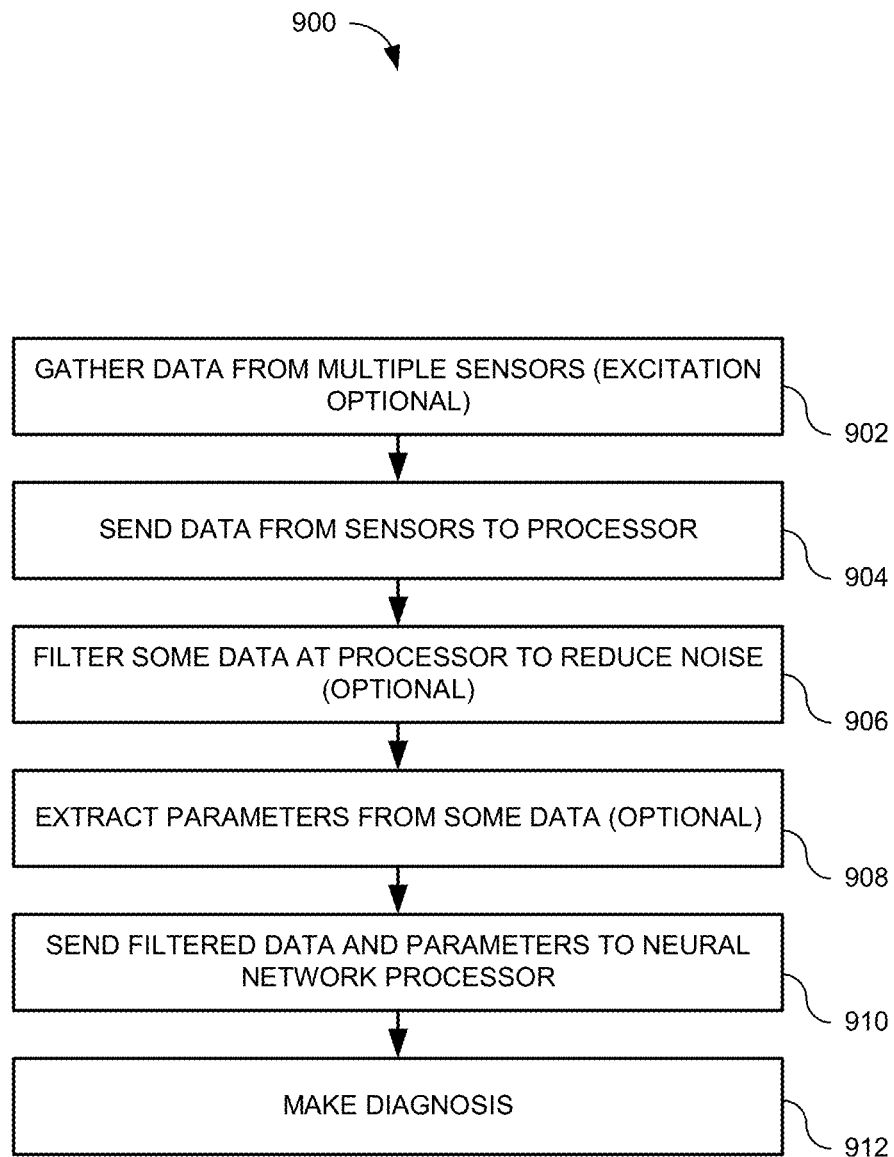
FIG. 9 illustrates a process for generating diagnoses and/or recommendations using artificial intelligence according to embodiments of the disclosed technology.

FIG. 9 illustrates a process 900 for generating diagnoses and/or recommendations using artificial intelligence according to embodiments of the disclosed technology. Depending on the implementation, the process 900 may include additional, fewer, or alternative elements, and the elements may be performed in various orders or in parallel.

Referring to FIG. 9, data from multiple sensors may be collected, at 902. The mask may provide light, sound, physical or other type of stimulation at specific times during the data collection to trigger specific reactions from the patient.

The data from all of the sensors may be sent to a processor, at 904. At least some of the data is filtered to reduce noise, at 906. Some data may not require filtering. In some embodiments, none of the data is filtered. In other embodiments, all of the data is filtered. In still other embodiments, some of the data is filtered, and some of the data is left unfiltered.

Some of the data may be further processed to extract relevant parameters, at 908. This reduces the amount of data that is passed on to the neural network. For example, high resolution image data captured by the cameras at 60 frames per second for 15 seconds may be too much data, so extracting the size of the pupil or other parameters may be advantageous.

The filtered data and extracted parameters may be sent to the neural network, at 910. The neural network may be used to make a diagnosis and/or a recommendation based on the collected data, at 912. In addition, data from previous measurements and diagnoses may be used to determine trends to supplement the new diagnosis, or to provide predictions based on the health trends.

In some embodiments, sensors are incorporated to measure immediate environment conditions and location including temperature, humidity, pressure, $CO/CO_2$ levels, altitude, location, and the like that could provide additional information to support diagnosis. For example, in the case of heat stroke, high altitude sickness, or nonventilated rooms, the environment conditions could provide additional information to supplement the diagnosis.

In some embodiments, the camera may be used to image the iris of the eye to identify the patient. This allows the measurement to be securely associated only with a specific individual and allows secure access to that individual's previous measurement data and diagnoses to supplement the present diagnosis.

Figure 10:
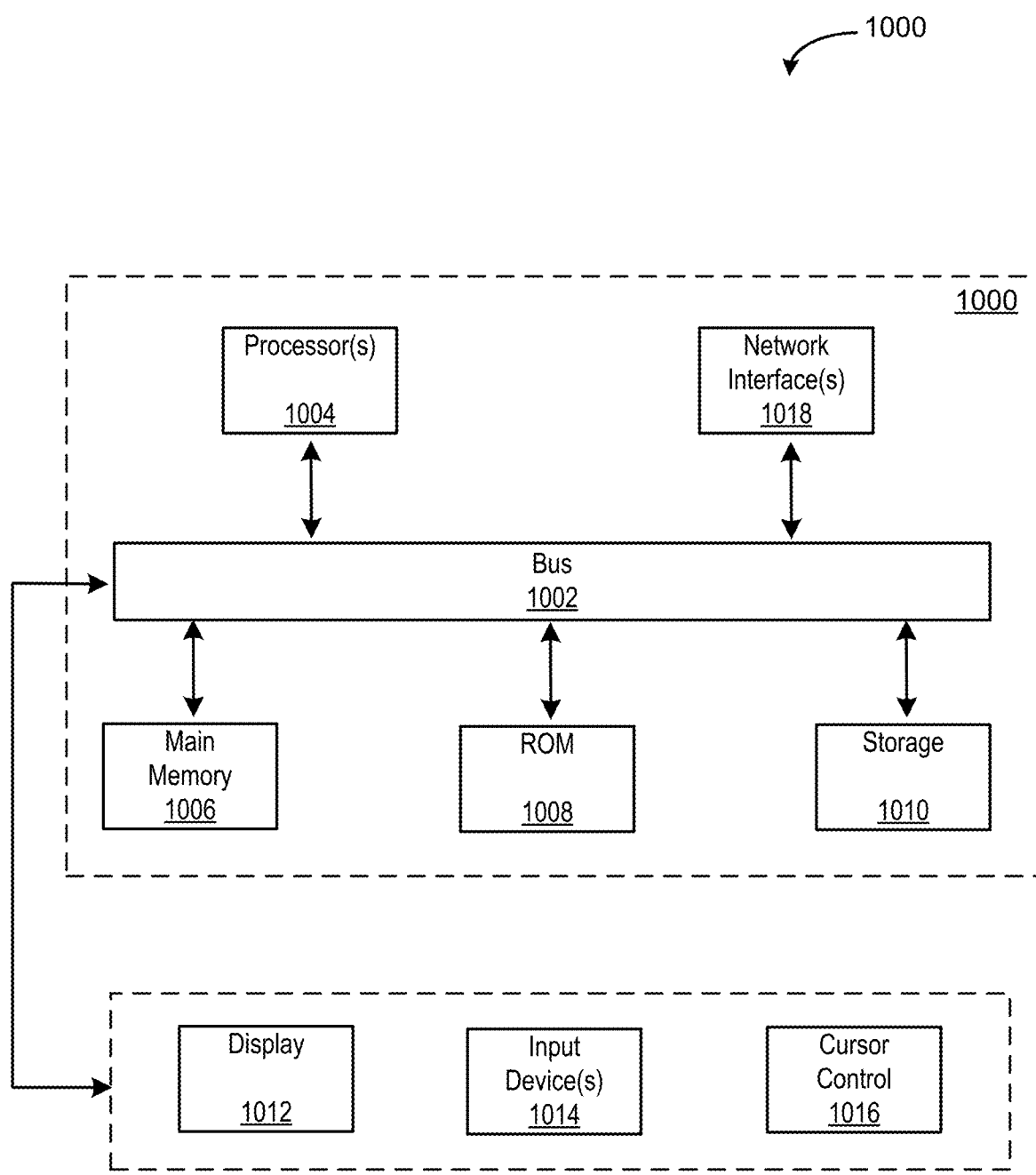
FIG. 10 depicts a block diagram of an example computer system in which embodiments described herein may be implemented.

FIG. 10 depicts a block diagram of an example computer system 1000 in which embodiments described herein may be implemented. The computer system 1000 includes a bus 1002 or other communication mechanism for communicating information, one or more hardware processors 1004 coupled with bus 1002 for processing information. Hardware processor(s) 1004 may be, for example, one or more general purpose microprocessors.

The computer system 1000 also includes a main memory 1006, such as a random access memory (RAM), cache and/or other dynamic storage devices, coupled to bus 1002 for storing information and instructions to be executed by processor 1004. Main memory 1006 also may be used for storing temporary variables or other intermediate information during execution of instructions to be executed by processor 1004. Such instructions, when stored in storage media accessible to processor 1004, render computer system 1000 into a special-purpose machine that is customized to perform the operations specified in the instructions.

The computer system 1000 further includes a read only memory (ROM) 1008 or other static storage device coupled to bus 1002 for storing static information and instructions for processor 1004. A storage device 1010, such as a magnetic disk, optical disk, or USB thumb drive (Flash drive), etc., is provided and coupled to bus 1002 for storing information and instructions.

The computer system 1000 may be coupled via bus 1002 to a display 1012, such as a liquid crystal display (LCD) (or touch screen), for displaying information to a computer user. An input device 1014, including alphanumeric and other keys, is coupled to bus 1002 for communicating information and command selections to processor 1004. Another type of user input device is cursor control 1016, such as a mouse, a trackball, or cursor direction keys for communicating direction information and command selections to processor 1004 and for controlling cursor movement on display 1012. In some embodiments, the same direction information and command selections as cursor control may be implemented via receiving touches on a touch screen without a cursor.

The computing system 1000 may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "component," "engine," "system," "database," data store," and the like, as used herein, can refer to logic embodied in hardware or firmware, or to a collection of software instructions, possibly having entry and exit points, written in a programming language, such as, for example, Java, C or C++. A software component may be compiled and linked into an executable program, installed in a dynamic link library, or may be written in an interpreted programming language such as, for example, BASIC, Perl, or Python. It will be appreciated that software components may be callable from other components or from themselves, and/or may be invoked in response to detected events or interrupts. Software components configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware components may be comprised of connected logic units, such as gates and flip-flops, and/or may be comprised of programmable units, such as programmable gate arrays or processors.

The computer system 1000 may implement the techniques described herein using customized hard-wired logic, one or more ASICs or FPGAs, firmware and/or program logic which in combination with the computer system causes or programs computer system 1000 to be a special-purpose machine. According to one embodiment, the techniques herein are performed by computer system 1000 in response to processor(s) 1004 executing one or more sequences of one or more instructions contained in main memory 1006. Such instructions may be read into main memory 1006 from another storage medium, such as storage device 1010. Execution of the sequences of instructions contained in main memory 1006 causes processor(s) 1004 to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, such as storage device 1010. Volatile media includes dynamic memory, such as main memory 1006. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between non-transitory media. For example, transmission media includes coaxial cables, copper wire and fiber optics, including the wires that comprise bus 1002. Transmission media can also take the form of acoustic or light waves, such as those generated during radio-wave and infra-red data communications.

The computer system 1000 also includes a communication interface 1018 coupled to bus 1002. Network interface 1018 provides a two-way data communication coupling to one or more network links that are connected to one or more local networks. For example, communication interface 1018 may be an integrated services digital network (ISDN) card, cable modem, satellite modem, or a modem to provide a data communication connection to a corresponding type of telephone line. As another example, network interface 1018 may be a local area network (LAN) card to provide a data communication connection to a compatible LAN (or a WAN component to communicate with a WAN). Wireless links may also be implemented. In any such implementation, network interface 1018 sends and receives electrical, electromagnetic or optical signals that carry digital data streams representing various types of information.

A network link typically provides data communication through one or more networks to other data devices. For example, a network link may provide a connection through local network to a host computer or to data equipment operated by an Internet Service Provider (ISP). The ISP in turn provides data communication services through the world wide packet data communication network now commonly referred to as the "Internet." Local network and Internet both use electrical, electromagnetic or optical signals that carry digital data streams. The signals through the various networks and the signals on network link and through communication interface 1018, which carry the digital data to and from computer system 1000, are example forms of transmission media.

The computer system 1000 can send messages and receive data, including program code, through the network(s), network link and communication interface 1018. In the Internet example, a server might transmit a requested code for an application program through the Internet, the ISP, the local network, and the communication interface 1018.

The received code may be executed by processor 1004 as it is received, and/or stored in storage device 1010, or other non-volatile storage for later execution.

Each of the processes, methods, and algorithms described in the preceding sections may be embodied in, and fully or partially automated by, code components executed by one or more computer systems or computer processors comprising computer hardware. The one or more computer systems or computer processors may also operate to support performance of the relevant operations in a "cloud computing" environment or as a "software as a service" (SaaS). The processes and algorithms may be implemented partially or wholly in application-specific circuitry. The various features and processes described above may be used independently of one another, or may be combined in various ways. Different combinations and sub-combinations are intended to fall within the scope of this disclosure, and certain method or process blocks may be omitted in some implementations. The methods and processes described herein are also not limited to any particular sequence, and the blocks or states relating thereto can be performed in other sequences that are appropriate, or may be performed in parallel, or in some other manner. Blocks or states may be added to or removed from the disclosed example embodiments. The performance of certain of the operations or processes may be distributed among computer systems or computers processors, not only residing within a single machine, but deployed across a number of machines.

As used herein, a circuit might be implemented utilizing any form of hardware, or a combination of hardware and software. For example, one or more processors, controllers, ASICs, PLAs, PALs, CPLDs, FPGAs, logical components, software routines or other mechanisms might be implemented to make up a circuit. In implementation, the various circuits described herein might be implemented as discrete circuits or the functions and features described can be shared in part or in total among one or more circuits. Even though various features or elements of functionality may be individually described or claimed as separate circuits, these features and functionality can be shared among one or more common circuits, and such description shall not require or imply that separate circuits are required to implement such features or functionality. Where a circuit is implemented in whole or in part using software, such software can be implemented to operate with a computing or processing system capable of carrying out the functionality described with respect thereto, such as computer system 1000.

As used herein, the term "or" may be construed in either an inclusive or exclusive sense. Moreover, the description of resources, operations, or structures in the singular shall not be read to exclude the plural. Conditional language, such as, among others, "can," "could," "might," or "may," unless specifically stated otherwise, or otherwise understood within the context as used, is generally intended to convey that certain embodiments include, while other embodiments do not include, certain features, elements and/or steps.

Terms and phrases used in this document, and variations thereof, unless otherwise expressly stated, should be construed as open ended as opposed to limiting. Adjectives such as "conventional," "traditional," "normal," "standard," "known," and terms of similar meaning should not be construed as limiting the item described to a given time period or to an item available as of a given time, but instead should be read to encompass conventional, traditional, normal, or standard technologies that may be available or known now or at any time in the future. The presence of broadening words and phrases such as "one or more," "at least," "but not limited to" or other like phrases in some instances shall not be read to mean that the narrower case is intended or required in instances where such broadening phrases may be absent.

We have just described some possible embodiments of the disclosure. One skilled in the art will recognize there are many other embodiments of the invention that are still within the scope of the claims below.

What is claimed is:

1. A diagnostic system, comprising:
a hardware processor; and
a non-transitory machine-readable storage medium encoded with instructions executable by the hardware processor to perform a diagnostic method comprising:
collecting data from a plurality of sensors in a mask placed on a face of a patient such that the mask covers both eyes of the patient, the data representing a plurality of health signs of the patient and immediate environment conditions, wherein at least one of the plurality of health signs relates to the patient's eyes, and wherein the mask does not include a device to secure the mask to a head of the patient;
causing a signal to be transmitted from the mask, the signal representing the data representing the plurality of health signs and the immediate environment conditions;
obtaining a diagnosis from a further signal received into the mask, the diagnosis being determined based on the plurality of health signs and the immediate environment conditions;
providing the diagnosis to the patient on a display screen disposed on an interior of the mask; and
displaying the diagnosis on an exterior surface of the mask.

2. The diagnostic system of claim 1, wherein:
the plurality of sensors comprises a camera to monitor the patient's eyes during controlled light excitation; and
the mask encloses the patient's eyes to control light reaching the patient's eyes.

3. The diagnostic system of claim 1, the diagnostic method further comprising:
determining a placement of the mask on the patient; and
providing guidance to the patient regarding the placement of the mask.

4. The diagnostic system of claim 1, the diagnostic method further comprising:
controlling one or more stimulus circuits in the mask to provide one or more stimuli to the patient, wherein the plurality of health signs include a reaction of the patient to the stimuli.

5. The diagnostic system of claim 1, wherein:
the diagnosis is determined using a neural network.

6. A non-transitory machine-readable storage medium encoded with instructions executable by a hardware processor of a computing component, the machine-readable storage medium comprising instructions to cause the hardware processor to perform a diagnostic method comprising:
collecting data from a plurality of sensors in a mask placed on a face of a patient such that the mask covers both eyes of the patient, the data representing a plurality of health signs of the patient and immediate environment conditions, wherein at least one of the plurality of health signs relates to the patient's eyes, and wherein the mask does not include a device to secure the mask to a head of the patient;
causing a signal to be transmitted from the mask, the signal representing the data representing the plurality of health signs and the immediate environment conditions;
obtaining a diagnosis from a further signal received into the mask, the diagnosis being determined based on the plurality of health signs and the immediate environment conditions;
providing the diagnosis to the patient on a display screen disposed on an interior of the mask; and
displaying the diagnosis on an exterior surface of the mask.

7. The non-transitory machine-readable storage medium of claim 6, wherein:
the plurality of sensors comprises a camera to monitor the patient's eyes during controlled light excitation; and
the mask encloses the patient's eyes to control light reaching the patient's eyes.

8. The non-transitory machine-readable storage medium of claim 6, the diagnostic method further comprising:
determining a placement of the mask on the patient; and
providing guidance to the patient regarding the placement of the mask.

9. The non-transitory machine-readable storage medium of claim 6, the diagnostic method further comprising:
controlling one or more stimulus circuits in the mask to provide one or more stimuli to the patient, wherein the plurality of health signs include a reaction of the patient to the stimuli.

10. The non-transitory machine-readable storage medium of claim 6, wherein: the diagnosis is determined using a neural network.

11. A diagnostic method, comprising:
collecting data from a plurality of sensors in a mask placed on a face of a patient such that the mask covers both eyes of the patient, the data representing a plurality of health signs of the patient and immediate environment conditions, wherein at least one of the plurality of health signs relates to the patient's eyes, and wherein the mask does not include a device to secure the mask to a head of the patient;
transmitting a signal from the mask, the signal representing the data representing the plurality of health signs and the immediate environment conditions;
receiving a further signal into the mask, the further signal representing a diagnosis, the diagnosis being determined based on the plurality of health signs and the immediate environment conditions;
providing the diagnosis to the patient on a display screen disposed on an interior of the mask; and
displaying the diagnosis on an exterior surface of the mask.

12. The diagnostic method of claim 11, wherein:
the plurality of sensors comprises a camera to monitor the patient's eyes during controlled light excitation; and
the mask encloses the patient's eyes to control light reaching the patient's eyes.

13. The diagnostic method of claim 11, further comprising:
placing the mask on the patient's face such that the mask covers the patient's eyes.

14. The diagnostic method of claim 11, further comprising:
determining a placement of the mask on the patient; and
providing guidance to the patient regarding the placement of the mask.

15. The diagnostic method of claim 11, further comprising:
controlling one or more stimulus circuits in the mask to provide one or more stimuli to the patient, wherein the plurality of health signs include a reaction of the patient to the stimuli.

16. The diagnostic method of claim 11, wherein:
the diagnosis is determined using a neural network.

* * * * *